US010682090B2

(12) United States Patent
Johnson et al.

(10) Patent No.: US 10,682,090 B2
(45) Date of Patent: Jun. 16, 2020

(54) SENSING DEVICE FOR CONTROLLING THE DELIVERY OF CARE TO IMMOBILE PATIENTS

(71) Applicant: General Electric Company, Schenectady, NY (US)

(72) Inventors: Christopher Donald Johnson, Clifton Park, NY (US); Peter Henry Tu, Niskayuna, NY (US); Andrew Phelps Day, Newtown, PA (US); Ting Yu, San Francisco, CA (US)

(73) Assignee: General Electric Company, Schenectady, NY (US)

( * ) Notice: Subject to any disclaimer, the term of this patent is extended or adjusted under 35 U.S.C. 154(b) by 728 days.

(21) Appl. No.: 15/197,151

(22) Filed: Jun. 29, 2016

(65) Prior Publication Data

US 2018/0000407 A1 Jan. 4, 2018

(51) Int. Cl.
*A61B 5/00* (2006.01)
*A61B 5/11* (2006.01)
(Continued)

(52) U.S. Cl.
CPC ............ *A61B 5/447* (2013.01); *A61B 5/0077* (2013.01); *A61B 5/0507* (2013.01);
(Continued)

(58) Field of Classification Search
CPC ..... A61B 5/447; A61B 5/0077; A61B 5/0507; A61B 5/1126; A61B 5/1128;
(Continued)

(56) References Cited

U.S. PATENT DOCUMENTS 5,993,400 A 11/1999 Rincoe et al.
6,384,728 B1 5/2002 Kanor et al.
(Continued)

FOREIGN PATENT DOCUMENTS

CN 1762856 A 4/2006
EP 2 014 892 A1 1/2009
(Continued)

OTHER PUBLICATIONS

Xu, Chi et al. "Mimo space-delay adaptive processing for wide-area indoor human motion classification." IEEE Transactions on Aerospace and Electronic Systems 52.3 (2016): 1384-1398. (Year: 2016).*

(Continued)

*Primary Examiner* — Devin B Henson
(74) *Attorney, Agent, or Firm* — Hanley, Flight and Zimmerman, LLC (57) ABSTRACT

The present disclosure relates to the reduction of pressure ulcers and falls with respect to patients with physical or cognitive impairments who are in bed. A control system assures that the bed and ancillary apparatus are physically set and that patient behaviors are responded to by care providers. Motion is monitored with a non-mutually exclusive portfolio of sensors, and this information is used by one or more reasoning engines. An integrated clinical workflow is informed by the patterns of movement and then the physical environment, patient interaction, and care provider workflow are controlled to reduce the incidence of falls and pressure ulcers in bed ridden patients.

17 Claims, 10 Drawing Sheets

(51) Int. Cl.
*A61B 5/05* (2006.01)
*G01S 13/88* (2006.01)

(52) U.S. Cl.
CPC .......... *A61B 5/1126* (2013.01); *A61B 5/1128* (2013.01); *A61B 5/7264* (2013.01); *A61B 5/746* (2013.01); *G01S 13/88* (2013.01); *A61B 5/1122* (2013.01); *A61B 5/6891* (2013.01); *A61B 2562/0252* (2013.01)

(58) Field of Classification Search
CPC ... A61B 5/7264; A61B 5/6892; A61B 5/1115; A61B 5/746; A61B 5/6891; A61B 5/6894; A61B 5/1036; A61B 2562/0247; A61B 2562/0252; A61B 2562/0257; G01S 13/58; G01S 13/88
See application file for complete search history.

(56) References Cited

U.S. PATENT DOCUMENTS

| | | | |
|---|---|---|---|
| 6,544,200 | B1 | 4/2003 | Smith et al. |
| 6,897,781 | B2 | 5/2005 | Cooper et al. |
| 7,030,764 | B2 | 4/2006 | Smith et al. |
| 7,378,975 | B1 | 5/2008 | Smith et al. |
| 8,027,849 | B2 | 9/2011 | Johnson et al. |
| 8,998,830 | B2 | 4/2015 | Halperin et al. |
| 2004/0046668 | A1* | 3/2004 | Smith .................. A61B 5/1115 340/573.7 |
| 2009/0099480 | A1 | 4/2009 | Salgo et al. |
| 2011/0043630 | A1* | 2/2011 | McClure ............. A61B 5/1116 348/143 |
| 2012/0026308 | A1* | 2/2012 | Johnson ............. G06K 9/00369 348/77 |
| 2012/0065547 | A1 | 3/2012 | Hann |
| 2012/0075464 | A1 | 3/2012 | Derenne et al. |
| 2012/0078144 | A1 | 3/2012 | Sinykin |
| 2012/0154582 | A1* | 6/2012 | Johnson ................ G06F 19/321 348/143 |
| 2013/0091631 | A1 | 4/2013 | Hayes et al. |
| 2013/0246088 | A1 | 9/2013 | Huster et al. |
| 2013/0317399 | A1 | 11/2013 | Ribble et al. |
| 2014/0257057 | A1 | 9/2014 | Reis Cunha et al. |
| 2015/0109442 | A1* | 4/2015 | Derenne .................. G06F 16/78 348/143 |
| 2015/0141762 | A1* | 5/2015 | Heinrich .............. A61B 5/1128 600/301 |
| 2015/0254956 | A1 | 9/2015 | Shen et al. |

FOREIGN PATENT DOCUMENTS

| | | |
|---|---|---|
| EP | 2 392 304 A1 | 12/2011 |
| EP | 2 715 695 A1 | 4/2014 |
| JP | 2009-125812 A | 6/2009 |
| WO | 2007/149934 A2 | 12/2007 |

OTHER PUBLICATIONS

"Smart mattress cover prevents bed sores", The Engineer, Retrieved from Internet URL: http://www.theengineer.co.uk/news/smart-mattress-cover-prevents-bed-sores/1003138, on Nov. 27, 2013, p. 1 (Jun. 24, 2010).

Xu, C., et al.,"MIMO Space-Delay Adaptive Processing for Wide-Area Indoor Human Motion Classification", IEEE Transactions on Aerospace and Electronic Systems, vol. 52, Issue 3, pp. 1384-1398 (Jun. 2016).

Invitation to Pay Additional Fees issued in connection with corresponding PCT Application No. PCT/US2017/037598, dated Sep. 21, 2017.

International Search Report and Written Opinion issued in connection with corresponding PCT Application No. PCT/US2017/037598, dated Nov. 21, 2017.

Kittipanya-Ngam, Panachit, et al.; "Computer vision applications for patients monitoring system", Information Fusion (FUSION), 2012 15th International Conference on, pp. 2201-2208, Jul. 9-12, 2012, Singapore.

Vilas-Boas, Maria C., et al.; "Monitoring of bedridden patients: Development of a fall detection tool", Engineering in Medicine and Biology Society (EMBC), 2013 35th Annual International Conference of the IEEE, pp. 4742-4745, Jul. 3-7, 2013, Osaka.

* cited by examiner

SENSING DEVICE FOR CONTROLLING THE DELIVERY OF CARE TO IMMOBILE PATIENTS

BACKGROUND

The subject matter disclosed herein relates to adverse event reduction in the absence of direct, continuous human observation and hands on interaction.

Pressure ulcers form when weight is concentrated in one or more areas over time, such as when a patient is relatively immobile. In particular, pressure ulcers develop when the skin's structure loses its healthy resilience and blood circulation is inadequate. Patients in a weakened condition laying in a bed where their body weight tends to concentrate in a particular location, such as, for example, a hip can be susceptible to developing pressure ulcers. While pressure ulcers for certain patient population are not avoidable, clinical guideline and practice suggest that moving the patient's body orientation from time to time allows the movement of body weight to other pressure points, lowering the probability of pressure ulcer development.

With this in mind, a pressure ulcer prevention or treatment protocol may stipulate that, for example, a patient is to be re-oriented every hour or at some other defined interval. An underlying assumption of such a protocol is that certain patients may be immobile and therefore are not moving on their own accord. An example case would be a sedated patient on a ventilator. When the risk for ulcers is clearly identified, care providers can implement and manage the pressure ulcer protocol(s), such as by routinely adjusting the resting position of the patient.

In addition, a patient who is susceptible to the condition but who is not properly identified as being so or who is not properly managed (whether or not properly identified as being at risk) may be susceptible to pressure ulcers or other adverse events due to failure to adhere to the appropriate care and prevention protocols. Hence, monitoring and implementation of such a protocol may be an issue.

BRIEF DESCRIPTION

In one embodiment, a protocol compliance sensing system is provided. In accordance with this embodiment, the protocol compliance sensing system includes a sensing system configured to detect skin surfaces of a patient using one or both of optical or range sensors, to detect movement patterns that concentrate pressure on the skin of the patient, and to generate an alert based on when the detected movement patterns are inconsistent with compliance with a pressure ulcer protocol.

In a further embodiment, a protocol compliance sensing system is provided. In accordance with this embodiment, the protocol compliance sensing system includes: a multimodality sensing system, comprising: a first sensing modality configured to detect skin surfaces of a patient using one or both of optical or range sensors, a second sensing modality configured to determine a centroid of mass of the patient; and a protocol adherence component configured to use both the detected skin surface and the centroid to detect movement patterns that concentrate pressure on the skin of the patient, and to generate an alert based on when the detected movement patterns are inconsistent with compliance with a pressure ulcer protocol.

In another embodiment, a patient management system is provided. In accordance with this embodiment, the patient management system includes: a classifying component configured to assign one or more patients into respective cohorts and to continuously or periodically assess placement of the one or more patients in the respective cohorts; a data integration component configured to receive and process one or more of protocol compliance data, patient characteristic data, or wound characteristics data from one or more sensor systems configured to monitor the one or more patients and to generate an assessment of each patients performance with a presently assigned cohort; and a communication component configured to provide feedback to the one or more patients based on the generated assessments.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present approach relates to approaches for assessing patient motion with respect to a protocol or other standard. In certain implementations, the motion is assessed using a multi-modality sensing arrangement suitable for sensing or assessing motion in various contexts that may be complementary to one another (e.g., providing qualitatively distinct motion information) such as measurements related to both a centroid of patient mass and a skin surface (external bound or boundary) of the patient. Further, sensor data from different modalities may be assessed in different manners so as to facilitate motion determination, such as using motion queues to determine relative motion of a surface in a computer vision context or a grid of squares or cubes to determine motion using ranging techniques (e.g., Doppler radar).

Such a system may be used to validate that a patient has been moved on a prescribed schedule by assessing and/or tracking the observed movement or activity relative to a protocol or schedule indicating the needed movement by the patient to avoid pressure ulcers or some other movement related condition. Non-compliance with the protocol or schedule may result in a notification, such as a message, alert, or other indicator, being provided to a caregiver. Such a notification may be made via a visual or audible notification channel or message prompting a caregiver to reorient the patient.

In certain implementations, motion sensing using systems as described herein may be used in the providing care over groups or cohorts of patients. By way of example, sensing and assessment techniques described herein may be used in the characterization of patients into different treatment or monitoring, in the ongoing assessment of maintaining or moving patients within or between such cohorts, and in approaches for incentivizing patient participation in protocol compliance efforts and/or self-healing or self-treatment programs. By way of example, movement and/or compliance information acquired using sensing systems as described herein may be used by computer-implemented treatment or assessment systems which may use one or more of patient's physical descriptors, indications of tissue health and/or healing, and care protocols, to determine the care plans and actions most likely to improve tissue health for the patient and/or for similarly attributed patients. Such systems may then group like patients into cohorts having similar or the same treatment regime and may monitor patient progress to assess whether a given patient is properly placed or should be moved to a different treatment cohort. Further, such approaches may provide feedback or incentives to patient to encourage patient compliance with treatment protocols and, in turn, patient healing.

Though a healthcare context is used in the present examples, the present approach may be utilized in other contexts where similar issues may arise, including but not limited to veterinary contexts, home health contexts, and mechanical apparatus contexts.

With respect to certain context provided below in explaining the present approach, the present disclosure incorporates the following references, in their entirety and for all purposes, as well as other references listed below: "SYSTEM AND METHOD FOR PROTOCOL ADHERENCE", published as U.S. Patent Application No. 2012/0154582; "SYSTEM AND METHOD TO SCHEDULE RESOURCES IN DELIVERY OF HEALTHCARE TO A PATIENT", issued as U.S. Pat. No. 8,027,849; and "SYSTEM AND METHOD TO MANAGE DELIVERY OF HEALTHCARE TO A PATIENT", published as U.S. Patent Application No. 2009/0089093, some or all of which may aid in the understanding of certain concepts discussed herein.

Figure 1:
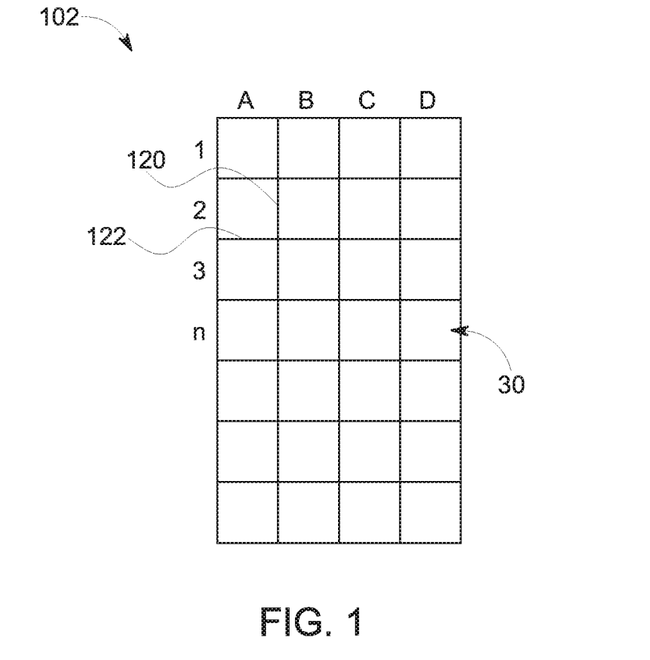
FIG. 1 depicts a configurable orientation grid for use with respect to a patient in a sensing environment, in accordance with aspects of the present disclosure.

In accordance with these approaches, various examples of motion measurement and assessment approaches are described below to provide useful context with respect to protocol adherence approaches as discussed herein. By way of example, FIGS. 1-4, depict aspects of a patient pressure ulcer measurement system as discussed herein. These aspects may include, but are not limited to, sensing and processing components configured to: map monitored movement onto a configurable orientation grid corresponding to or framed about a patient orientation such as, for example, a bed 102 (as shown in FIG. 1); generate and/or update motion queues generated using an anatomical locator with respect to a patient 100; measure a tissue health, such as using a tissue health measuring sequence; map motion outcomes over time 74 (FIG. 3); generate and/or track a granular mapping of patient and care features; generate and/or update a temporal understanding (e.g., time chart or graph 24) of outcomes (FIG. 4) as a function of patient and care features; and generate and/or monitor a body of evidence to improve clinical decisioning relating to improving tissue health. Various examples of the use of these motion aspects are provided below to facilitate explanation.

Using an example of a patient bed 102 (as seen from above in FIG. 1) as one orientation and venue for patient care, in certain motion related aspects the physical space is divided into selectable granulations, such as a grid 30 specified by horizontal line 120 and vertical line 122 increments. In one implementation, such as an implementation employing a computer vision and or a range sensing component, for each unit of time, motion of the patient surfaces as sensed using computer vision and/or range sensing observations of the patient and relative to the grid 30 are recorded.

In one such implementation, the placement and degree of the granularity defined by lines 120, 122 is a set point in the system. This placement and granularity of the grid 30, as defined by lines 120, 122 may be configured and/or adjusted to achieve a balance between detection specificity and acquisition of sufficient data for computation of momentum, motion, surface contour of the body and bed. Likewise, the relevant time units over which motion is assessed or aggregated relative to grid elements, and which define another dimensional aspect of the system, may be configured and/or adjusted to achieve a desired level of sensitivity and responsiveness.

Figure 2A:
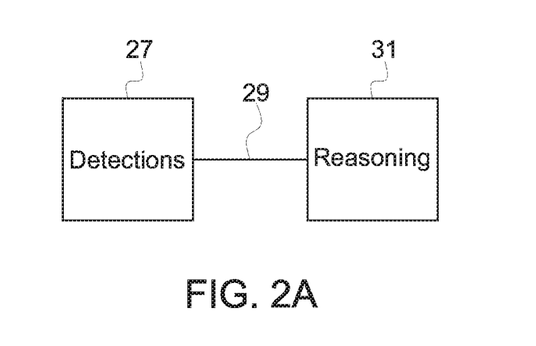
FIG. 2A depicts detection and reasoning aspects of a protocol compliance implementation, in accordance with aspects of the present disclosure.
Figure 2B:
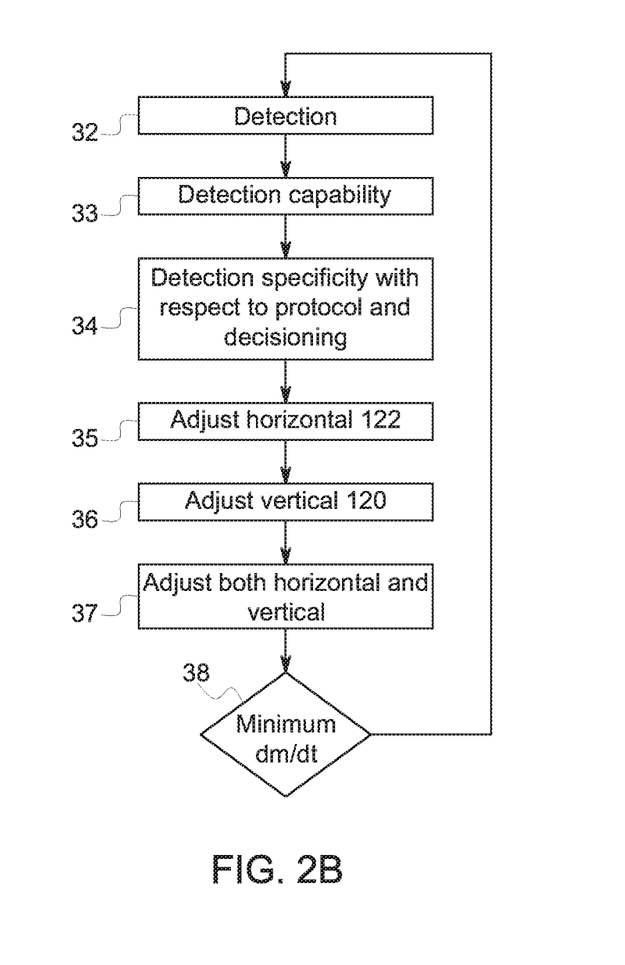
FIG. 2B depicts a process flow for determining detection granularity, in accordance with aspects of the present disclosure.

By way of example, and turning to FIG. 2A, the a detection system (i.e., detections 27) generates observations 29 (e.g., computer vision observations) with respect to grid 30 with respect to the patient 100 (shown below) and/or bed 102 provide optical information, depth information (e.g., in the case of a range sensing modality), or both and the protocol compliance system reasons 31 what the motion and surface contours within the spatial grid 130 mean with respect to the clinical guidelines or protocols prescribed for the patient. The process (FIG. 2B) of determining detection granularity in x-, y-, and z-dimensions is comprised of a movement detection 32 resolved from the sensing and reasoning 29, 31 and subsequently processed over an adjustable interval of time to determine 33 that movement is detected. Detection in this context is a collection of observations 200 sufficient to differentiate one detection zone (defined by lines 120, 122) from another. Detection specificity 34 with respect to the protocol and decisioning state estimation capability may be assessed in terms of the actual patient being moved or the apparatus and its settings being set up in a calibration exercise. The horizontals 35 are moved through a gradient as are the verticals 36 and then concurrent 37. Optionally, a height (e.g., elevation) 121 in x-, y-, and z-dimensions is likewise adjusted by a response optimizing function 38 which requires a minimum threshold of detected movement vectors per unit time and seeks the highest specificity in a grid 30 or cube over a time interval of clinical interest.

Figure 3:
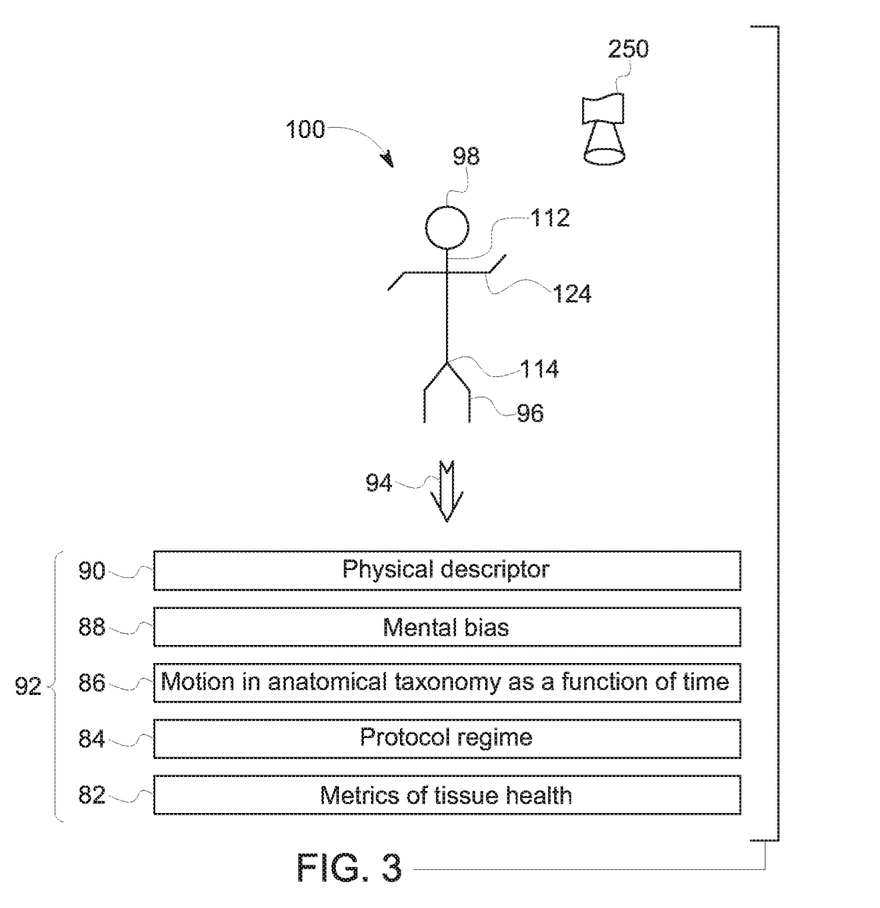
FIG. 3 depicts motion outcomes mapped over time, in accordance with aspects of the present disclosure.

In certain implementations, motion queues may be created when a relative change in position occurs (e.g., a change in the position of two patient surfaces (such as may be determined by a computer vision system) relative to one another, such as at flexible parts of the human body), as shown in FIG. 3. In the depicted example, the patient's head 98 orients through the neck 112, or hands 124 through a wrist, or thigh 96 through a hip 114. The bodies orientation is recorded as relative changes in joint movements as determined from the patient surfaces. It is this movement, reasoned via a computer vision system, that is recorded within the bed grid loci defined by horizontal and vertical axes 120, 122. Thus, in such an implementation, the computer vision system calculates changes in pixelated images attained by an optical sensor 250 (or other suitable modality) and calculates the relative movements of the patient 100.

As noted above, in certain implementations the sensing and protocol adherence system may develop customized or patient-specific care plans or may classify different patients into different cohorts based on patient characteristics, where each cohort receives is handled in view of a protocol adapted to the characteristics shared by the members of the respective cohort. In such an approach, and turning to FIG. 3, patients are characterized (process flow arrow 94) by descriptive attributes 92 for the purposes of classifying each patient into a suitable cohort for monitoring and/or treatment. Examples of suitable characterization attributes include: (a) physical descriptors 90, such as age, weight, sex, skin fragility, and prior ulcers; (b) mental bias 88 such as passive, interactive, alert, compliant, working to avoid ulcers, dementia; (c) motion 86 in anatomical taxonomy as a function of time which, by anatomical component of the body (e.g., head, neck, elbow, wrists, hands, hips, knees, ankles, feet) sum the motion queues; (d) current or actual protocol regime 84 being followed with specificity as to motions desired and achieved along with time and clinical support provided; and (e) metrics 82 of tissue health which may be quantitative or qualitative scores or values corresponding to clinical indicators and the testing protocol and devices used to attain these skin and tissue health clinical readings. For example, in one implementation the clinical indicators may be a measured or assessed state or status of one or more wounds being monitored.

These five factors which range from physical descriptors 90 of the patient 100, to a patient's mental state 88, actual motion 86 by body anatomical location, the care protocol 84 and clinical measures 82 of tissue health may be used to assess the comparative effectiveness of care plans or protocols, both at the patient and cohort level, so that the presently discussed method of improving tissue health is continuously improved in terms of weight density over time for areas of the body and patterns of loading for ever more specific guidance based upon these attributes. In certain implementations, regression and data mining are used to correlate the comparative effectiveness and designs of experiments to enrich these classifiers, to identify outliers, and to routinely reassess patient classifications into respective cohorts.

As noted above, with respect to the acquired and tracked data and its use in patient and cohort assessment, in certain implementations it is a goal to reduce the rate of clinical decline and to enable more rapid clinical indicator outcome improvement. With this in mind, and turning to FIG. 4, a clinical indicator 80 that is quantifiable and repeatable and which may be attained by a suitable tissue health sensing modality, such as an industry accepted measuring system (e.g., optical measuring, ranging, and so forth) may be mapped to a scale of tissue vitality 78. The patient's clinical outcome is recorded (here represented collectively by data lines 76) and monitored over time 74.

Figure 4:
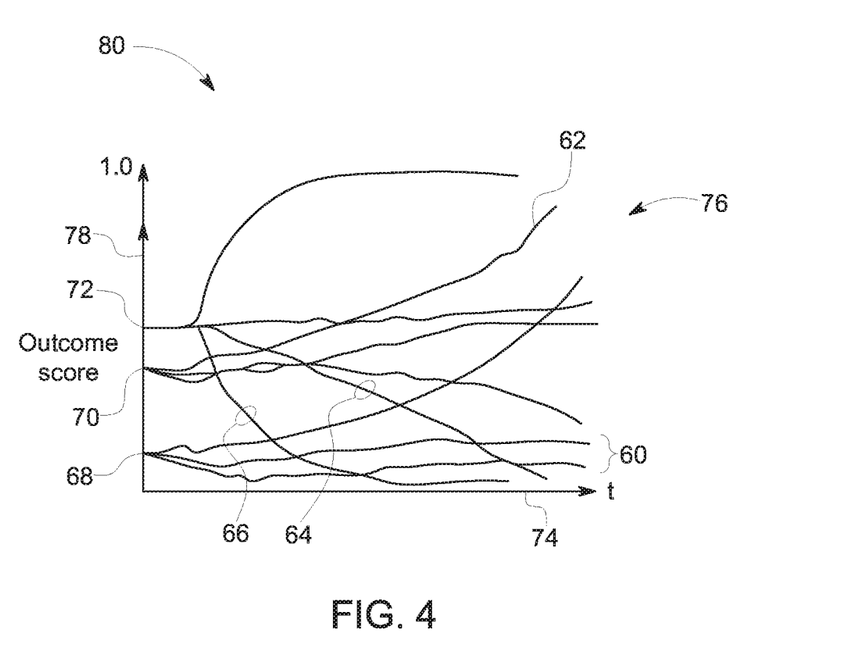
FIG. 4 depicts a temporal mapping of outcomes as a function of patient and care features, in accordance with aspects of the present disclosure.

Three example initial condition clinical outcomes are described to illustrate the clinical outcome objectives of the disclosed invention. A first patient 72 presents with tissue health indicator 78 of 0.5, a second patient 70 presents with a 0.4 indicator, and a third patient 68 begins at 0.1. In the depicted example, third patient 68 has significantly less tissue health in a given anatomical location than first patient 72 does. As tissue health is a local indicator specific to an anatomical location, these temporal indicators are also local. The indicator can be a cumulative one for the patient or specific to one area of the body. There may be a plurality of concurrent indicators for the same patient. First patient 72 with comparatively superior tissue health on, as an example, their hip than third patient 68, it can be appreciated that the reverse could be the case for an upper body indication where third patient 68 has a tissue health measure in that area that is superior to that of first patient 72.

Using a first patient 72 as an example, in certain implementations it is a goal to avoid a rapid deterioration 66 of tissue health from which clinical recovery becomes significantly more challenging than in other contexts, such as a slow or gradual rate of decline 64. Said positively, a goal is to rapidly improve or increase 62 the clinical outcome at the highest rate achievable. With this in mind, assignment of a patient to a cohort and/or assignment (or customization) of a care protocol to a patient may be based on such considerations and taking into account other patient specific factors, such as those noted above, so as to achieve the best outcome.

It can be appreciated that the time scale 74 may be on the order of days for an acute inpatient condition and on the order of months or years for patients 100 in therapy or assisted living. A longer duration patient, for example, may be third patient 68 who is held stable (lines 60) over a year even at a reduced vitality, but does not degenerate. In such a scenario, the patient may be able to attain improvement (e.g., line 62) through monitoring and adherence to care protocols in response to actual clinical state, as discussed herein.

While tissue degradation is localized and specific to an individual patient 100, it can be appreciated that impacting (e.g., improving) a broader cohort's health may also desirable. For example, improvement of the health of a larger cohort may include cohorts such as some or all patients in a hospital, an insured population, residents in assisted living, or any other meaningful aggregation of patients (such as based upon similar physical or demographic characteristics, movement limitations, wound susceptibility, and so forth) where there is a desire to focus on pressure ulcer reduction tissue health improvement and an allocation of resources is made to effect the desired change.

Figure 5:
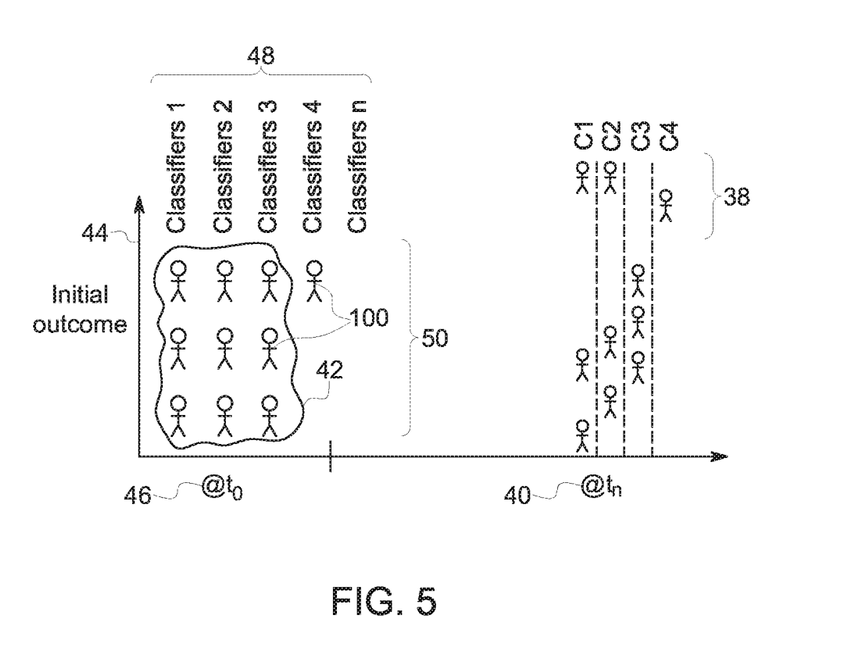
FIG. 5 depicts a graphical representation of a health impact and comparative learning implementation, in accordance with aspects of the present disclosure.

With this in mind, turning to FIG. 5, a further example of a broad health impact and of comparative learning is also provided. For example, a cohort 50 may be defined by a set of one or more classifiers 48 which can be, as an example, physical descriptors 90, mental bias 88, motion as a function of time 86, protocol regime 84, tissue health 82 (e.g., descriptive attributes 92, discussed above), and/or a cohort of interest, which could be a patient population being cared for, insured groups, or patients undergoing a common monitoring or experimental regime. The individual patients 100 are mapped at an initial time 46 by their various classifiers 48 with respect to their clinical indication 44. In one embodiment, an aim is to raise the sample cohort's health by treating combinations or clusters of patients 100 in a classified pool of like attributes (e.g., group 42) and raise the health of that group using tailored protocols which may be comparatively tested in a design of experiment or more precisely managed with a stable specific protocol. One or more of these clusters 42 of patients may be managed in order to efficiently raise the health of a broader population of interest.

In the depicted example, at a time period 40 later than an initial time period 46, the clinical conditions are again mapped by attribute for the patient population being monitored. Patients of like classifiers 48 who comparatively raise their clinical outcome an order of magnitude of statistical significance (e.g., patients 38) may be assessed and used to refine treatment, monitoring, and/or protocol aspects (e.g., setting the grid 30 sizes being monitored, the type of clinical measure, the frequency, pattern, and duration of rotation, the allowed weight loading and its duration, the effectiveness of patient room setup, and/or care aides such as foam fittings or vibratory or pressure distribution apparatus) for current or future cohorts of similarly attributed patients.

Figure 6:
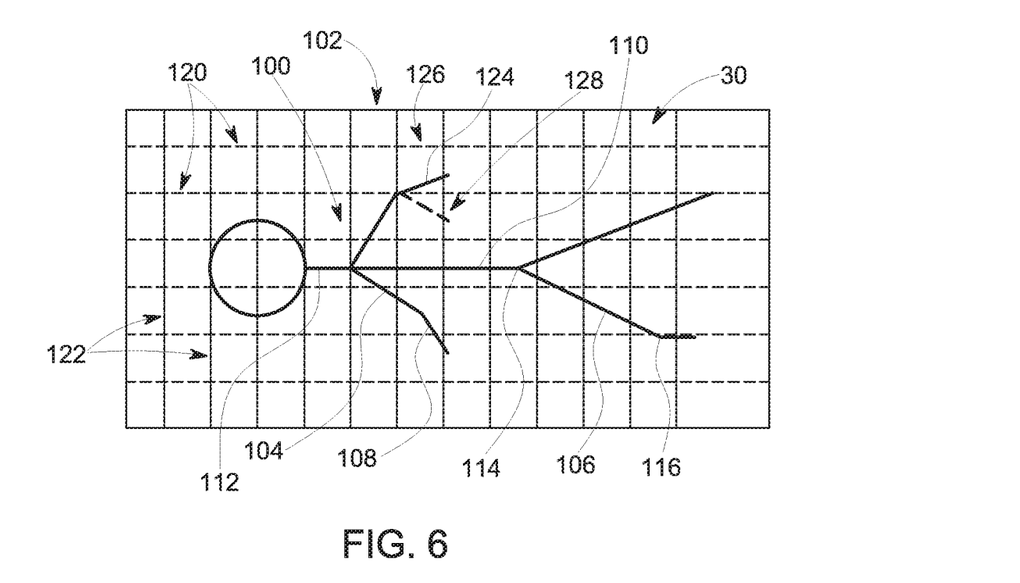
FIG. 6 depicts a patient and bed in the context of a configurable grid, in accordance with aspects of the present disclosure.

With the preceding in mind, certain motion-monitoring or assessment aspects of the present approach discussed with respect to FIGS. 1-5 are described in additional detail. Turning to FIG. 6, in the context of a patient care scenario, the present approach may be useful in reducing or preventing development of pressure ulcers by a patient 100 who spends substantial amounts of time in a confined circumstance such as a bed 102. With respect to this depiction, various motion aspects useful in assessing sufficiency of patient movement within a given time period are described below.

Linear Motion: A first motion aspect for use in conjunction with the present approach is the detection of linear motion. In one implementation, changes in displacement of the patient body parts are optically sensed using a sensing system. Similarly, height profile change may be measured using a ranging aspect of the system (i.e., a ranging system). Body mass placement may be inferred from augmentation of the optical and/or range derived position (using the optical and/or ranging systems noted above) with the incorporation of sensors such as load cells and pressure pads, and so forth. Such measurements in this context, regardless of the sensing mechanism(s) employed, may constitute measures of linear motion.

For example, in an optical sensing (e.g., computer vision) implementation, the exact surfaces of skin and the orientations of limbs and digits of the body are detected with respect to the geometry of the bed and related apparatus. This is in contrast to other approaches, such as pressure pads, load cells, RFID, and centroid detection in computer vision, which all merely approximate relative location of the patient based on some surrogate measure (e.g., a centroid or central mass measurement). In this manner, the actual placement or position of the patient's boundary (e.g., skin surface) may be determined as opposed to a more generalized measure of patient placement, such as a center of mass. In such an implementation, the optical sensing approach enables precise spatial relationships to be determined and evaluated based on the physical boundaries of the patient surfaces.

It can be appreciated that for optical methods that resolve surface location and movement, a patient in bed may have occluded visibility such as from blankets and thus the person's physical boundaries may not be resolvable. This limitation may be overcome by using the shape profiles of what can be observed and momentum vectors, if available, to infer with statistical and machine learning techniques as to what the skin contact locations are as learned on the present and prior humans which have been used to train the system.

Another sensing approach is Doppler-based, which may provide range or elevation type information corresponding to patient surfaces or boundaries. A Doppler-based sensing device may be placed above the patient 100, such as in a light fixture, above a ceiling tile, or mounted on a ceiling or wall or behind a wall. The Doppler-based system may also be placed below the patient or aside the patient. Depending on the Doppler-based sensing device, there may be multiple sensing elements (i.e., sensors) and the sensors may be coupled, as in the computer vision based sensing discussed above, to resolve the precise boundaries of patient surfaces, such as skin, and the exact geometrical location of such surfaces.

In response to the actual physical boundaries of patient surfaces and the monitored motion of such surfaces, and in view of defined pressure ulcer prevention protocol definitions and sequences, one or more instructions or notifications may be automatically issued to control mechanical or computational assets or prompt care providers.

Turning back to FIG. 6 a patient 100 is depicted in a hospital bed 102 with arms 104 and legs 106 in an articulated orientation (i.e., having segments, here limb segments, connected by joints) corresponding to elbow 108, waist 110, neck 112, hips 114, and knees 116. In one implementation, the patient's articulated orientation can be computed based on skin surfaces as measured at one instant of time or in multiple instances of time, where each instance establishes the positional state of the patient 100 and bed 102, and the changes between these positional states enables the calculation of motion. In certain implementations, the plane of the bed is divided into control volumes (i.e., grid 30) depicted horizontally with lines 120 and vertically with lines 122. Portions of the patient's body (e.g., limbs, head, torso, joints) move through these monitored control volumes over time, facilitating assessment and measurement of motion by optical sensing and/or tracking.

The zones defined by lines 120, 122 are defined virtually and the patient 100 is tracked within these zones and as their determined surfaces traverse different zones, such as for example a hand 124 moving to zone 128 from zone 126. In one implementation, the movements of a patient 100 are detectable by the superimposition of the patient's body parts within these zone areas and between these zones. For the case of optical sensing, the patient body parts visible to the sensing system are used and in the case of range sensing, the heights of the patient's body parts may be used. In addition to the optical and range sensing observable location, the incorporation of other sensing modalities is used if available, such as Doppler, load cells and pressure pads, as discussed in greater detail below.

In an implementation employing an optical sensor to detect linear motion associated with one or more body parts, a spatio-temporal image filter may be applied to the body parts imaged by the sensor to detect the localized extremes of the filtering response pattern. In one such example, the spatio-temporal image filter is biologically inspired (i.e., is based on how biological systems sense and interpret motion) and engineered to resemble how human visual cortex system detects and recognizes human body motions and actions.

Figure 7:
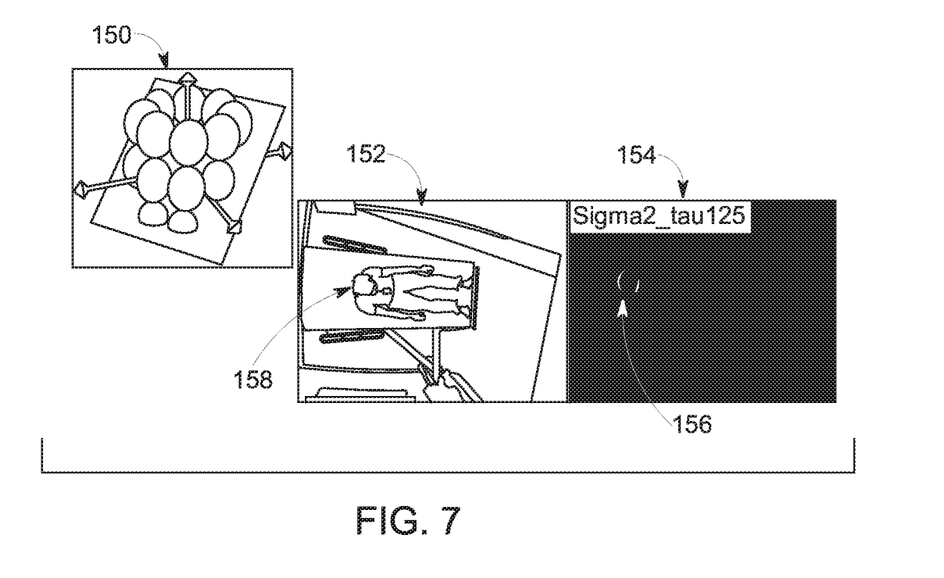
FIG. 7 depicts an implementation of a spatio-temporal filter, in accordance with aspects of the present disclosure.

A spatio-temporal image filter may be implemented based on a stationary sensor setup, as shown in the image sequence of FIG. 7. This is consistent with approaches where the camera-based or Doppler based pressure ulcer system is deployed in a patient room. As shown in FIG. 7, a separable spatio-temporal filter bank 150 may be applied to the video imagery or ranges 152 to obtain the response surfaces 154 where displayed intensity corresponds to perceived motion. For example, in response imagery 154, low intensity (i.e., white or light regions) correspond to motion extent (here a patient raising his head) and high intensity (i.e., black or dark regions) correspond to lack of perceived motion.

Thus, as shown in FIG. 7, from such a filtering response image 154, local maxima (light region 156) can be detected and used as linear motion indicator associated with the body parts 158 (here a patient head undergoing motion, such as being raised). While such a spatio-temporal filter may be designed to produce maximum response to repetitive motions, it may also be responsive to more complex forms of motion.

Figure 8:
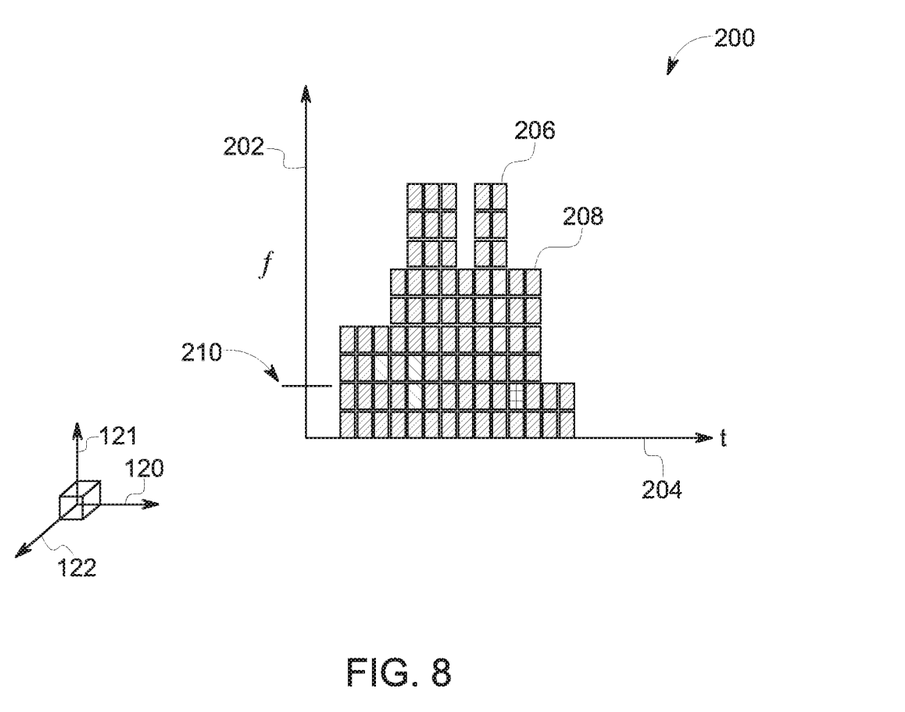
FIG. 8 depicts zone movement data tracked along multiple axes, in accordance with aspects of the present disclosure.

Turning to FIG. 7, in one implementation based on the arrangement shown in FIG. 6 and using optical sensing and/or Doppler methodology, such as discussed with respect to FIG. 8, the individual zone movements are recorded over some period of time (e.g. 1 hour, 6 hours, 12 hours, 18 hours, 1 day, 3 days, 1 week, and so forth). As shown in FIG. 8, zone movement data 200 is shown tracked along multiple (e.g., two or three) axes, with time t depicted on the x-axis. In this example, a zone is defined by the coordinates established using virtual lines 120 and 122 (and or elevation 121) to detect movement at a unit of time. The zones defined by virtual lines 120, 122 (and/or elevation 121) may be adjusted (e.g., the spacing and/or number of lines) so as to achieve greater or lesser degrees of granularity for the monitored area. By one example, in one implementation, the areas defined by the line 120, 122 (i.e., the zone areas) and/or the sampling times are adjusted to provide suitable motion and time measurements for a given patient.

The matrix of zones are evaluated, for a given observation period, to encode the patient's body parts movement within the matrix (e.g., grid). In an example embodiment, the zones where movement has occurred are recorded and accumulated along the y-axis 202 of FIG. 8. When the next interval of time progresses, the calculation repeats so as to provide data 200 over time. A pattern of linear motion is thus derived through time with respect to the x-axis (i.e., time axis) 204.

With this particular implementation in mind, it may be appreciated that as data from optical, Doppler, range, pressure pad, and/or load cells are collected, these data collection operations may be performed in continuous time at a prescribed sampling rate, across the finest granularity of sensing area for discrimination. In such an implementation, this raw data is then integrated over an adjustable time period over a post processed zone configuration, i.e., forming a spatio-temporal zone cue for feature data computation generated from the raw data. This may also facilitate pattern discovery and data mining for future set-points of zones and time differentials as well identifying precursor patterns that can be used to define or initiate an alarm condition for future pressure ulcer protocol settings.

Further, as noted above, in certain implementations the bed zones defined by lines 120, 122, an optional height designation or granulation (e.g., elevation 121) and the parts of a patient's body within a particular zone may be used to further characterize or classify which anatomic part(s) of the patient's body are moving. Thus, for example, the upper torso data 206 may be differentiated from the right hip data 208 in the tracked and graphed data 200. The patient's body parts preferably do not remain in the same zones defined by lines 120, 121, 122. Instead, it is expected or desired that a patient body would traverse many zones over time, thus indicating movement. Particular anatomic parts or joints of a patient's body may thus be monitored by specific tracking or by means of pattern recognition to uncover patterns of under-movement (i.e., insufficient movement with respect to a define protocol) by matching against an absolute or comparative cases from other like attributed patient data. Should insufficient movement be identified for a monitored body area (e.g., torso data 206, hip data 208, and so forth) relative to a set point 210 (the set point 210 being defined on an absolute or comparative basis), a clinical workflow 212 (shown in FIG. 5) is instantiated and triggered so as to cause the patient to be moved and/or to adjust the supporting area pressures with inflatable pressure pads, pillows and so forth controllable spatially so as to correspond with the monitored zones.

Figure 9:
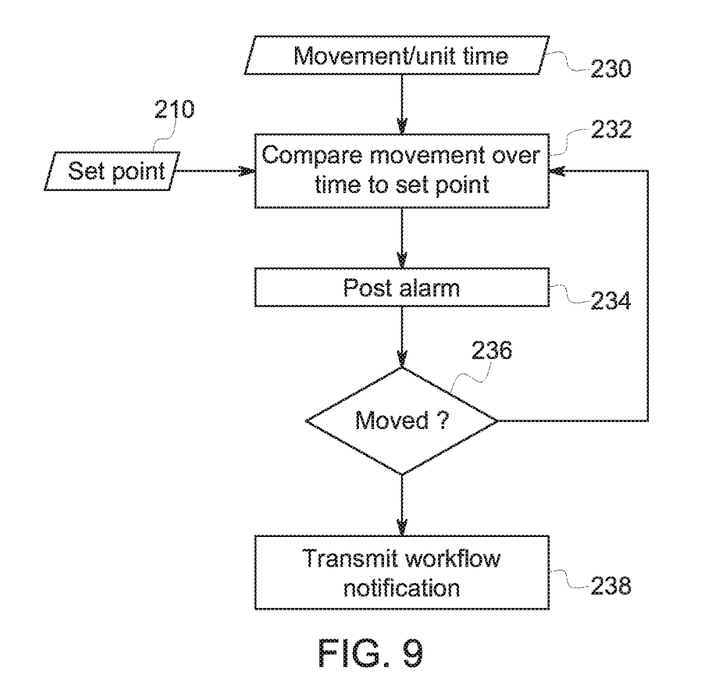
FIG. 9 depicts a process flow for providing workflow notifications, in accordance with aspects of the present disclosure.

As shown in FIG. 9, should the frequency and/or sufficiency of movement, expressed as a traversal of zones per unit time 230, fail to cross (comparison block 232) a specified threshold (e.g., set point 210), an alarm 234 is posted. When the patient moves (block 236), either by themselves in response to this alarm or via the assistance of a care giver, the alarm is reset and comparison resumes. If the patient does not move, a workflow queue notification is sent (block 238) to the clinical task management system which requests prioritized care workflows 215, such as disclosed by U.S. Patent Application No. 2012/0010901 titled "SYSTEM AND METHOD TO SCHEDULE RESOURCES IN DELIVERY OF HEALTHCARE OF A PATIENT", incorporated herein by reference in its entirety for all purposes. The alarming movement queues are reset upon abatement of the alarm.

Figure 10:
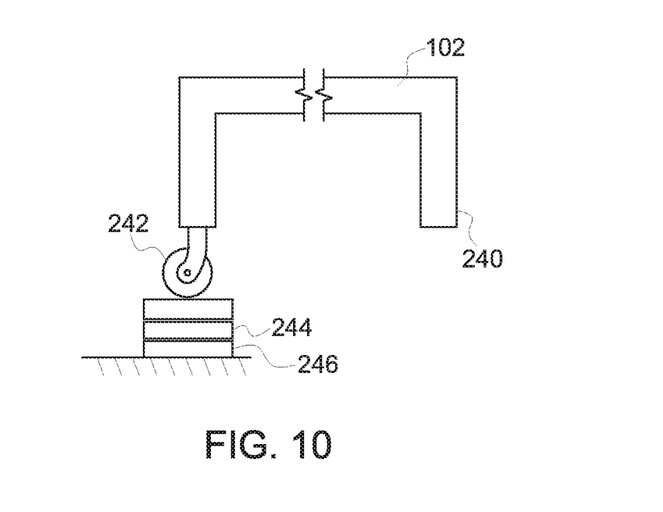
FIG. 10 depicts a load cell implementation in the context of a support structure, in accordance with aspects of the present disclosure.

Load Cells: In a second motion-related aspect, data from load cells provided as part of or with the patient bed 102 may be integrated into the measuring system. By way of example, load cells may be provided as part of the bed 102, such as above the wheels, under the wheels, and/or as part of the frame, as shown in FIG. 10. In particular, as depicted in FIG. 10, a structure used to support a patient 100 transmits load to a surface by means of a static member such as a leg 240 or wheel 242 of bed 102. In one such implementation, a static or dynamic load transmittal structure rests on a load cell 244 whose physical structure accepts the transmitted load in a stable way that prevents unanticipated movement. A base 246 rests on flooring in such a way as to stabilize the load cell 244 and protect the floor. The load cell 244 outputs an electrical or optical signal which may be converted into a digital signal indicative of the load measured at the cell at a given time. Various "pads" which use physical displacement of surfaces or springs or embedded sensors help measure position and weight on the support surface location, i.e., the surface of the bed 102 or other support.

Figure 11:
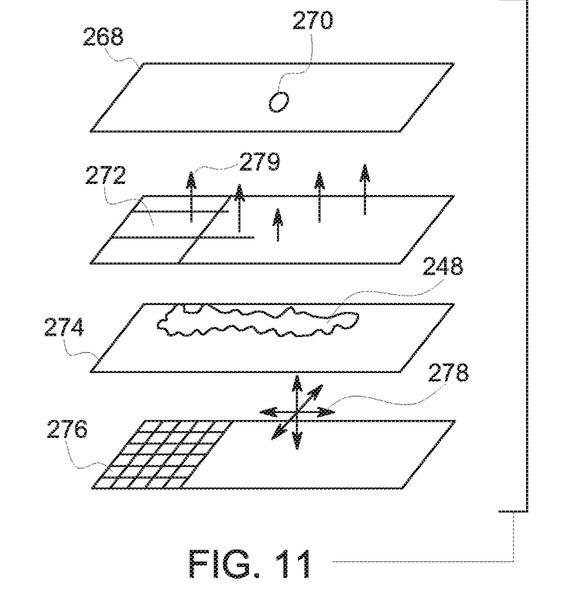
FIG. 11 depicts a load measuring operation in the context of a support surface, in accordance with aspects of the present disclosure.

By way of example of a load measuring operation using such structures, and turning to FIG. 11, on a support surface 268 is a pressure point 270 specific to a tissue degradation of a patient's anatomy whose healing is desired by the process of relaxing compression to that spot and allowing blood flow. In one system, the surface 268 where there is weight may be monitored by location 272 for the weight. A load cell based system 274 calculates a centroid 248 of mass. In certain implementations, the present system 276 develops motion queues 278 which are, in one embodiment, the differential rate of change of a specific contour (e.g., skin surface or boundary) in addition to a mass centroid, and in another embodiment, the aggregation of rates of change at body anatomy coupled with the centroid 248 change, point load change 279, and optical tracking on the body's form.

Positioning across the sensing mechanism uses the measures (e.g., pressure point 270, point load change 279, centroid 248 of mass, and/or motion queues 278, and not the absolute support surface x-y plane. The composite motion queue may be derived by changes in optical image pixilation of body features or Doppler ranges and is appended to by load points 279 from grid-based displacement measuring means and by mass centroid velocity, direction, and momentum, or specific skin surface velocity, direction and momentum.

With this in mind, in certain implementations where load cell data is employed, differential weight changes per unit time are employed to calculate the patient body weight centroid. The weight centroid may then be mapped with respect to the virtual zones (i.e., grid 30) defined by lines 120, 122. Inferences are achieved to relate centroid movement 248 to specific surface movement such as, for example, at a knee 281, using machine learning and deep learning.

In certain approaches the load cells 244 may be used without the benefit of optical or ranging sensing. However, in certain of the present implementations, the load cell information is collected along with the optical and ranging data discussed above to augment or establish movement patterns or trigger alarms, such as based upon the combination of centroid and skin surface data. The coordinate systems for the load cell and optical sensing or ranging data may be spatially aligned (such as by using a shared grid system defined by lines 120, 121, 122) to facilitate the combined use of such datasets. Alternatively, the outputs or derived measurements from the various sensing modalities may be used to jointly make a movement determination, such as by averaging or using a voting (e.g., majority voting) scheme.

Figure 12:
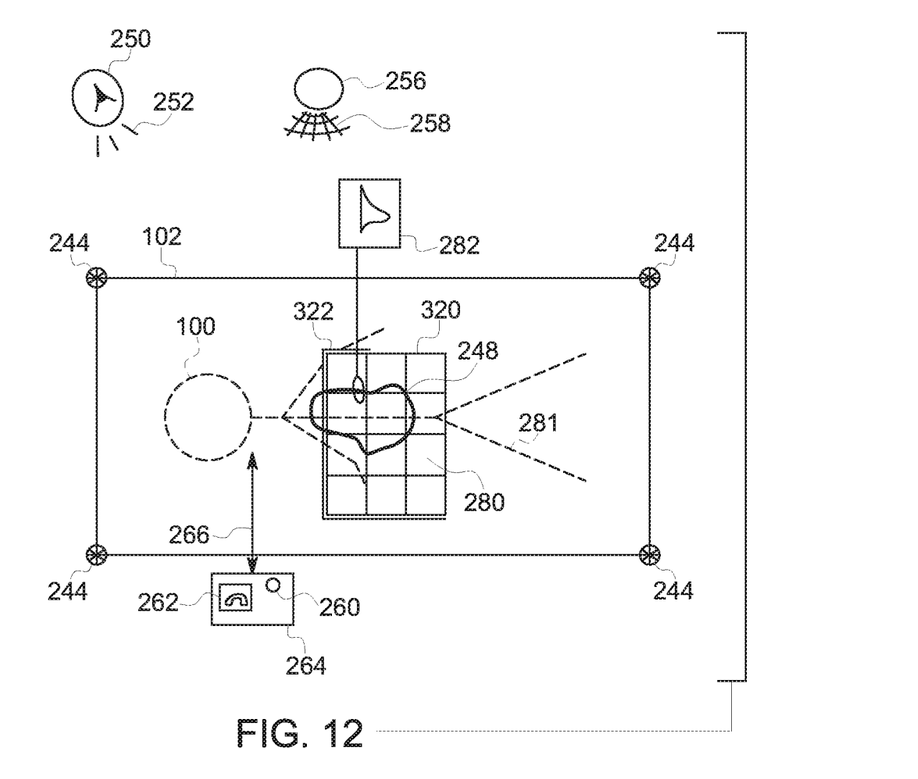
FIG. 12 depicts a mixed modality sensing system, in accordance with aspects of the present disclosure.

By way of example using the computer vision modality, though it can be appreciated that Doppler based range sizing would store these attributes, and turning to FIG. 12, an example of a mixed- or hybrid-data system is shown that includes acquisition of load cell data and skin surface data. In this example, computer vision 250 is employed to optically monitor 252 the bed 102 and patient 100, reasoning the patient's location and the body parts based on observed patient surfaces (as discussed above). In addition to or instead of computer vision 250, a range detection modality 256 may be provided to sense 258 distances to patient surfaces from the sensor to reason where the patient's location and the body parts are located based on the measured distances or elevations. These same modalities may also monitor other environmental aspects, such as bed height, guard rails, and locations of objects the patient may interact with, such as a glass 260 or phone 262 on a bedside table or mobile tray 264, which ideally is located within reach 266.

In the depicted example, the data provided by these modalities are augmented by the inclusion of load cells 244, as discussed above, which in the current example reconcile the body mass centroid 248 of a patient 100. Using a virtual grid 280 of the bed which is comprised of adjustable areas, the mass centroid 248 is calculated based on load cell measurements and is superimposed onto the geospatial map of the bed used by the optical and range sensing modalities and is accumulated over time. The integration of the load derived centroid 248 with respect to the explicit anatomic surface locations as derived by one or both of the optical 250 or ranging systems 256 can be accomplished through probabilistic sensor fusion 282 or by other suitable approaches. The principal behind this fusion is that the weight of a person is considered as a function of their body part mass distribution and orientation, which are computable from the optical and/or range sensing modalities. Over time, the integration of the mass derived centroid 248 and the exact optical and/or range sensing placement can be accomplished using the disclosed system. A centroid resolution for momentum estimation and exact surface characterization with range or computer vision are one suitable implementation.

Figure 13:
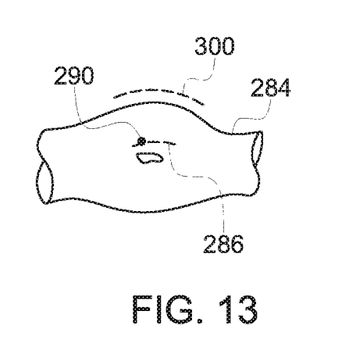
FIG. 13 depicts a body shape that may be observed using a sensing system, in accordance with aspects of the present disclosure.

With the preceding in mind, in this example an optical 250 and/or ranging 256 aspect computes placement of a body shape 284 (e.g., a limb or joint) (shown in FIG. 13) that may be observed to move relative to the geospatial grid 280. Concurrently, the mechanical centroid 248 of the body mass and bed 102 is calculated and, taking into account estimation uncertainty, positioned with respect to the grid 280. As movement occurs, the relative displacement of the centroid 286 is assumed to be consistent with what is observed by the other location modalities 250, 256 in terms of observed movement at each time instance. The combined data may then be used to derive a likely location 290 of the body shape 284. Relative velocities of the centroid are also derived, such as using the comparative load cell changes of weight 292 as a function of time and momentum is calculated. This change in momentum and direction 294, 296 are expressed as vectors which are filtered, along with location 300 at the prior time instant to fit the inferred position of the centroid 248.

Figure 14:
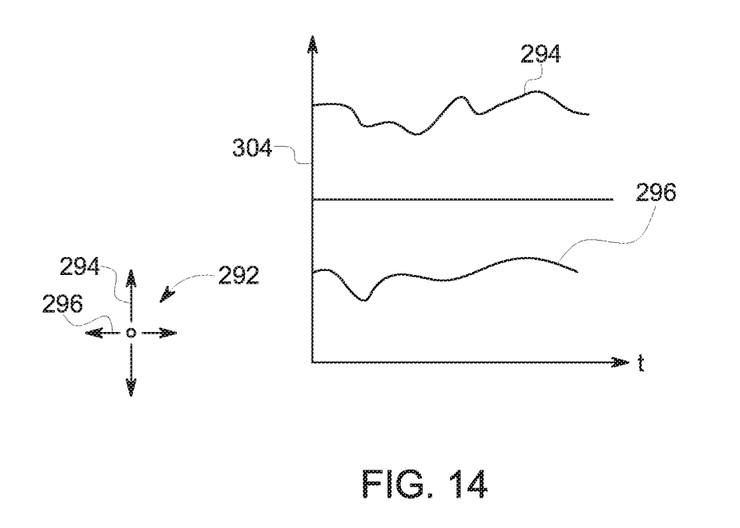
FIG. 14 graphically depicts momentum vectors tracked over time, in accordance with aspects of the present disclosure.

In one embodiment, as shown in the graph of FIG. 14, the momentum vectors 294, 296 are tracked 304 over time as part of the protocol assessment process. The positional change and momentum changes 294, 296 are accumulated over time t and monitored for relative movement and compared to a desired threshold or minimum (e.g., set point 210), enhancing the determination of movement as a function of mass, in addition to the positional estimate of a patient 100 derived solely from optical or ranging sensing modalities 250, 256 which do not by themselves establish mass or, therefore, changes in pressure which may be relevant to the development of pressure ulcers.

Figure 15:
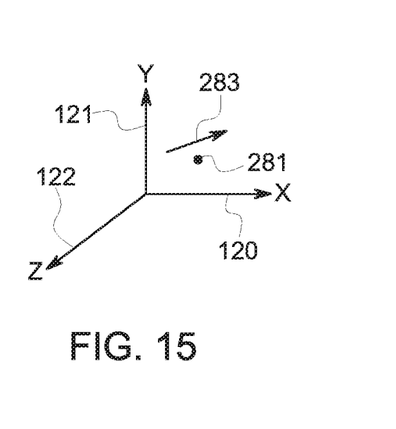
FIG. 15 depicts a momentum vector tracked over a time interval and compared to a physical location, in accordance with aspects of the present disclosure.

Turning to FIG. 15, the momentum vector over a time interval dt 283 is compared to a precise physical location 281 resolved with computer vision or Doppler sensing. The location 281 may be, for example, the pressure point under consideration. Its location/momentum relationship should itself, through time, have a plurality of orientations in a healthful situation where pressures are not exceeded or concentrated through time, these temporal momentum-spatial features are used to train response model with respect to outcome scores 78 in one or many patients, themselves stratified by features 92.

Pressure Pad Load Sensing: In a third motion-related aspect, pressure pad load sensing for the bed 102 may be integrated with other data for assessing pressure ulcer protocol compliance. In particular, pressure pads 320 are typically laid on the mattress, under the patient 100. As has been described above, aspects of the present approach may rely on or incorporate differential weight changes per unit time, determined using pressure pad load sensing, and map such changes from the monitored zones of the pad 320 to the zones defined by lines 120, 122 discussed above. In such an approach, load cells may be used to calculate location, velocity and pressure change as opposed to momentum change.

In one such approach the pressure pad information is collected along with one or both of optical 250 or ranging 256 data, in which case any of the monitored sensing modalities could establish movement patterns or trigger alarms. The orientation of the pressure pad's 322 load (pressure) sensing compared to the optical 250 or range sensing 256 location may be physically established by its mechanical orientation on the bed 102. Alternatively, the plurality of sensing modalities may be averaged or use a majority voting scheme to set the final determination.

Motion Queues: In a fourth motion-related aspect, motion queues may be employed to establish sufficiency of patient activity. The optical 250 and ranging 256 sensing modalities use changes of state of a unit of area per unit time to determine motion. This aspect is particularly useful in establishing movement at the intersection of body parts such as knee, hip, elbow, neck joints, torso twisting and head movements. In certain aspects, motion queues may be employed is assessing patient motion and to assess compliance with a pressure ulcer protocol. By way of example, the angular velocity for motion queues may be summed per unit time, per zone and then tabulated and reasoned over as discussed above, by leveraging machine learning approaches to discover the patterns of movements from the training data. The pressure ulcer protocol, requiring a shift of weight per unit time, is thus enabled.

Figure 16:
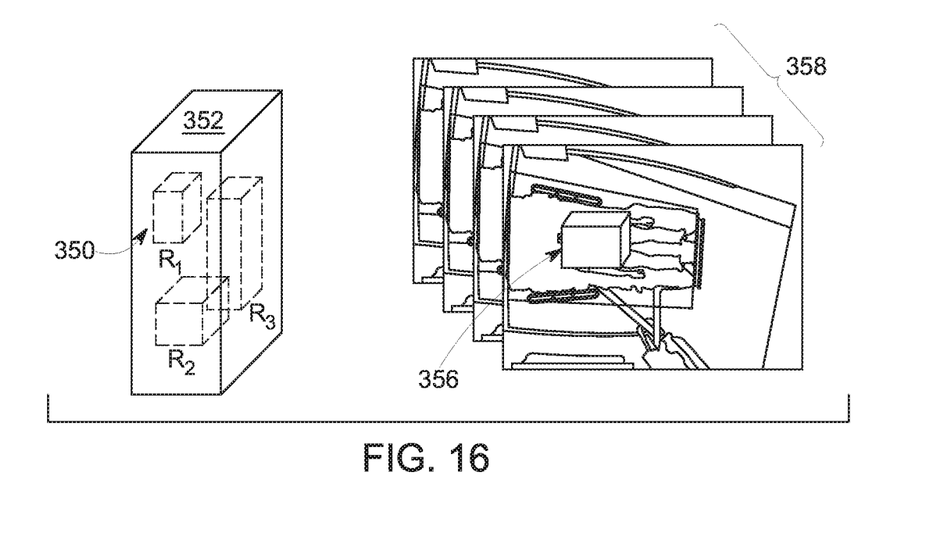
FIG. 16 depicts motion queues and motion activity data, in accordance with aspects of the present disclosure.

In one particular embodiment, the optical sensor 250 is used to compute the motion queues and their associated motion activity sample data generated from this queue is illustrated in FIG. 16. Neuroscience evidence from the human brain study suggests that instantaneous motion forms pathways over a temporal window, i.e., motion queue, as shown in the region of R1 (350), R2, R3 in 352, that contribute to the recognition of biological motion. Thus, in one embodiment one or both of motion and shape features can be extracted at each of the detected localized extremes of the filtering response pattern from the linear motion. In particular, the instantaneous motion features can be computed as 3-D spatial-temporal image features as discussed above with respect to linear motion. At the localized extreme of these features, i.e., interest points, the response variances can also been computed within the spatio-temporal rectangular volumes, 356, in the video queue 358, defined by a shape-context like descriptor. These local spatio-temporal rectangular volumes are first partitioned into log-polar sectors, and then the histogram for orientation in each sector is computed. To achieve efficient computation, integral image techniques can be applied to speed up this volumetric feature computation in such a motion queue.

Pattern Recognition and Machine Learning: In another motion-related aspect, patterns within zones and motion queues may be detected. These patterns may be used to further train pattern detection over time and/or over locations (such as between hospitals) via observed historical patient attributes to recognize the precursors of pressure ulcer formation. This learning aspect may determine how granular to set zones defined by lines 120, 122 based on differing patient characteristics (e.g., age, gender, and so forth), what the time differential is for movement detection and the alarming thresholds, and so forth by training the algorithms with the data collected over multiple hospitals across a variety of patient population.

Technical effects of the invention include a system that detects a movement or lack of movement (or pattern of movements) corresponding to a protocol of care, such as that prescribed by a medical doctor or a therapist and then triggers a response if the protocol is not adhered to. Movements may be detected and quantified either to one or more protocols or on an absolute measured movement basis. In one implementation, there may be multiple (e.g., 3, 4, 5, or 6) motion related aspects, each corresponding to a movement pattern associated with a patient being in a hospital or other bed.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A protocol compliance sensing system, comprising:
 at least one of an optical sensor or a range sensor to determine physical boundaries of skin surfaces of a patient;
 a load cell sensor to capture load cell measurements to determine a centroid of mass of the patient; and
 a computer processor to:
  detect movement patterns that concentrate pressure on the skin of the patient, the detected movement patterns determined from motion of the physical boundaries of the skin surfaces of the patient captured by the at least one of an optical sensor or a range sensor during an observation period;
  encode the movement patterns to a matrix of zones;
  determine weight concentration and momentum of the patient based on the centroid of mass of the patient and the encoded movement patterns; and
  generate an alert and a control instruction to trigger patient care when the detected movement patterns are determined to be inconsistent with compliance with a model of a pressure ulcer protocol based on an evaluation of the movement patterns encoded in the matrix of zones with respect to the determined weight concentration and momentum over a plurality of observation periods.

2. The protocol compliance sensing system of claim 1, wherein the at least one of an optical sensor or a range sensor includes an optical sensor, and wherein the computer processor is to implement a computer vision based sensing system using the optical sensor to detect the skin surfaces of the patient.

3. The protocol compliance sensing system of claim 1, wherein the at least one of an optical sensor or a range sensor includes a range sensor, and wherein the computer processor is to implement a range detecting system using the range sensor to detect the skin surfaces of the patient.

4. The protocol compliance sensing system of claim 3, wherein the range detecting system comprises a Doppler-based detecting system.

5. The protocol compliance sensing system of claim 1, wherein the computer processor is to classify the patient by one or more of a physical descriptor, a medical state, a rate of change of medical state, or a mental acuity to create a state estimator, wherein the classifying compares the state estimator with other patient states and creates one or more cohorts according to the classifications amongst a patient population.

6. The protocol compliance sensing system of claim 5, wherein the computer processor is further configured to assign the patient into respective cohorts and to continuously or periodically assess placement of the patient in the respective cohorts.

7. The protocol compliance sensing system of claim 5, wherein the computer processor is further configured to receive and process one or more of protocol compliance data, patient characteristic data, or wound characteristics data to generate an assessment of each patient's performance with a presently assigned cohort and to provide feedback to the patient based on the generated assessments.

8. The protocol compliance sensing system of claim 5, wherein the computer processor periodically changes a patient composition of the cohorts so as to most achieve a favorable clinical rate of change of the one or more patients.

9. The protocol compliance sensing system of claim 1, wherein the computer processor is configured to compare a location of some or all of the skin surfaces with physical attributes of a reference surface based on prescribed physical states and limits of an arrangement of the patient and reference surface.

10. A protocol compliance sensing system, comprising:
a multimodality sensing system, comprising:
  a first sensing modality configured to determine physical boundaries of skin surfaces of a patient using at least one of an optical sensor or a range sensor, and
  a second sensing modality configured to determine a centroid of mass of the patient; and
a computer processor configured to use both the determined physical boundaries of skin surfaces and the centroid of mass to:
  detect movement patterns that concentrate pressure on the skin of the patient, the detected movement patterns determined from motion of the physical boundaries of the skin surfaces of the patient captured by the at least one of an optical sensor or a range sensor during an observation period;
  encode the movement patterns to a matrix of zones; and
  determine weight concentration and momentum of the patient based on the centroid of mass and the encoded movement patterns; and
  generate an alert and a control instruction to trigger patient care when the detected movement patterns are determined to be inconsistent with compliance with a model of a pressure ulcer protocol based on an evaluation of the movement patterns encoded in the matrix of zones with respect to the determined weight concentration and momentum over a plurality of observation periods.

11. The protocol compliance sensing system of claim 10, wherein the first sensing modality comprises a computer vision based sensing system using at least one of the optical sensor or the range sensor to detect the skin surfaces of the patient.

12. The protocol compliance sensing system of claim 10, wherein the second sensing modality comprises a load cell based sensing system using load cells to detect the centroid.

13. The protocol compliance sensing system of claim 10, wherein the computer processor is configured to compare an observed and a calculated surface velocity of the skin surface in a two-dimensional (2D) or three-dimensional (3D) space with a momentum of the sensed centroid to determine compliance with the pressure ulcer protocol.

14. The protocol compliance sensing system of claim 10, wherein the computer processor fuses pressure sensing from weight pads of the second sensing modality with skin surface detected using one or both of computer vision or Doppler-based sensing of the first sensing modality to compare weight concentration and momentum, by anatomical location, against a criteria for one or more of weight, velocity and momentum.

15. The protocol compliance sensing system of claim 14, wherein the computer processor is further configured to trigger state estimation comparators in a defined protocol based on the fused pressure sensing and skin surface data.

16. The protocol compliance sensing system of claim 10, wherein the computer processor fuses pressure sensing from weight pads of the second sensing modality with skin surface detected using one or both of computer vision or Doppler-based sensing of the first sensing modality to determine weight concentration and momentum, by anatomical location, and to correlate weight, velocity and momentum against changes in a medical state of the patient.

17. The protocol compliance sensing system of claim 16, wherein the correlating is performed using an unsupervised learning algorithm.

* * * * *